United States Patent [19]

Hajima et al.

[11] Patent Number: 6,057,448
[45] Date of Patent: May 2, 2000

[54] PROCESS FOR PRODUCING IMIDAZOLE DERIVATIVES

[75] Inventors: Makoto Hajima, Hirakata; Yasuyuki Hozumi, Amagasaki; Mikio Kabaki, Ashiya, all of Japan

[73] Assignee: Shionogi & Co., Ltd., Japan

[21] Appl. No.: 09/319,700

[22] PCT Filed: Dec. 19, 1997

[86] PCT No.: PCT/JP97/04708

§ 371 Date: Jun. 10, 1999

§ 102(e) Date: Jun. 10, 1999

[87] PCT Pub. No.: WO98/29395

PCT Pub. Date: Jul. 9, 1998

[30] Foreign Application Priority Data

Dec. 26, 1996 [JP] Japan .................................. 8-347507

[51] Int. Cl.$^7$ .................................. C07D 401/00
[52] U.S. Cl. .................................. 546/274.4; 548/323.5; 548/324.1
[58] Field of Search .................. 548/323.5, 324.1; 546/274.4

[56] References Cited

FOREIGN PATENT DOCUMENTS

| | | |
|---|---|---|
| 63-316773 | 12/1988 | Japan . |
| 1-131163 | 5/1989 | Japan . |
| 3-89343 | 4/1991 | Japan . |
| 5-255270 | 10/1993 | Japan . |
| WO96/10019 | 4/1996 | WIPO . |

*Primary Examiner*—Joseph McKane

*Attorney, Agent, or Firm*—Wenderoth, Lind & Ponack, L.L.P.

[57] ABSTRACT

The present invention provides a process for producing a compound of the formula (III):

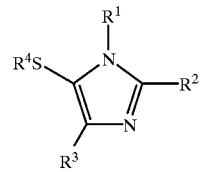

(III)

wherein $R^1$ and $R^3$ are independently hydrogen or an organic group; $R^2$ is an organic group; and $R^4$ is an optionally substituted aryl. by reacting the compound of formula (I):

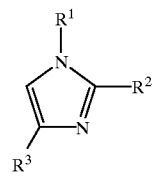

(I)

wherein $R^1$, $R^2$, and $R^3$ are as defined above, with the compound of formula (II):

$$R^4\text{—S—Hal} \quad\quad\quad (II)$$

wherein $R^4$ is as defined above and Hal is halogen, in the presence of base.

6 Claims, No Drawings

PROCESS FOR PRODUCING IMIDAZOLE DERIVATIVES

TECHNICAL FIELD

The present invention relates to a process for producing imidazole derivatives.

BACKGROUND ART

Various imidazole derivatives have been researched to apply them to medicines, and the present inventors found that the imidazole derivatives having an arylthio group at 5-position were efficient as an antiviral agent or an anti-HIV agent.

It is known, as a process for producing imidazole derivatives having a substituted thio group, that halogenated imidazole derivatives are reacted with mercaptane/NaH/DMF after formation of an imidazole ring (HETEROCYCLES, Vol 33, No 1, 21–26, (1992)). It is also known that imidazole derivatives are reacted with disulfide in the presence of a base after halogenation of —CH of the imidazole ring (J. Chem. Perkin Trans. I 1139–1145 (1989) and WO 96/10019). These methods are, however, inappropriate to the reaction on an industrial scale because they require halogenation of —CH of the imidazole ring and a strong base such as NaH or the like. As mentioned above, a process for producing imidazole derivatives having a substituted thio group, which is appropriate to convenient, economical, large-scaled production, has not been known heretofore.

DISCLOSURE OF INVENTION

The present inventors have intensively studied to develop convenient, economical, large-scaled production of substituted thio imidazole derivatives such as 5-arylthio imidazole derivatives, and succeeded in the reaction of imidazole derivatives of the following formula (I) with thiohalide of the formula (II) in the presence of a base to give imidazole derivatives having a substituted thio group of the formula (III). Thus, the present invention has been accomplished.

Accordingly, the present invention provides a process for producing a compound of the formula (III):

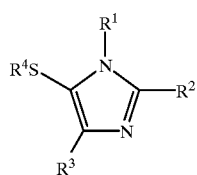
(III)

wherein $R^1$ and $R^3$ are independently hydrogen or an organic group; $R^2$ is an organic group; and $R^4$ is an optionally substituted aryl, which comprises reacting a compound of the formula (I):

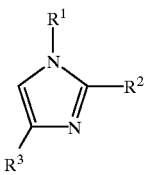
(I)

wherein $R^1$, $R^2$, and $R^3$ are as defined above, with a compound of the formula (II):

$$R^4—S—Hal \qquad (II)$$

wherein $R^4$ is as defined above and Hal is halogen, in the presence of a base.

BEST MODE FOR CARRYING OUT THE INVENTION

A preferable embodiment of the present invention includes the process wherein the organic groups in the formula (I) are an optionally substituted alkyl, an optionally substituted alkenyl, an optionally substituted aryl, an optionally substituted thioaryl, an optionally substituted heteroaryl, an optionally substituted heteroarylalkyl, an optionally substituted aralkyl, an optionally substituted acyl, an optionally substituted carbamoyl, an optionally substituted alkoxycarbonyl, —CH=NOH, —CH=NNH$_2$, or —A—X wherein A is —CH$_2$OCH$_2$— or —CH$_2$O— and X is an optionally substituted aryl or —COR$^5$ wherein R$^5$ is an optionally substituted alkyl, an optionally substituted alkoxy, an optionally substituted aryl, or an optionally substituted amino.

The more preferable embodiment of the present invention is (1) the process wherein $R^1$ is hydrogen or an optionally substituted heteroarylalkyl; $R^2$ is —A—X wherein A is —CH$_2$OCH$_2$— or —CH$_2$O— and X is an optionally substituted aryl or —COR$^5$ wherein R$^5$ is an optionally substituted alkyl, an optionally substituted alkoxy, an optionally substituted aryl, or an optionally substituted amino; and $R^3$ is an optionally substituted alkyl. In particular, the process for producing the compound wherein $R^1$ is optionally substituted pyridylmethyl (esp. pyridin-4-ylmethyl) is preferred. Especially, the process for the compound wherein $R^2$ is benzyloxymethyl, acetyloxymethyl, benzoyloxymethyl, methoxycarbonyloxymethyl, and carbamoyloxymethyl is preferred.

A preferable compound of the formula (II) is (2) 3,5-dichlorobenzenesulfenyl chloride.

A preferable base is (3) triethylamine or N-methylmorphorine.

The terms used in the present specification are defined below.

The term "organic group" refers to an optionally substituted alkyl, an optionally substituted alkenyl, an optionally substituted aryl, an optionally substituted arylthio, an optionally substituted heteroaryl, an optionally substituted heteroarylalkyl, an optionally substituted aralkyl, an optionally substituted acyl, an optionally substituted carbamoyl, an optionally substituted alkoxycarbonyl, —CH=NOH, —CH=NNH$_2$, —A—X wherein A is —CH$_2$OCH$_2$— or —CH$_2$O— and X is an optionally substituted aryl or —COR$^5$ wherein R$^5$ is an optionally substituted alkyl, an optionally substituted alkoxy, an optionally substituted aryl, or an optionally substituted amino, and the like.

The term "alkyl" means a C1–C20 straight or branched chain alkyl, for example, methyl, ethyl, n-propyl, i-prolyl, n-butyl, i-butyl, t-butyl, n-pentyl, i-pentyl, n-hexyl, n-heptyl, n-octyl, n-nonyl, n-decyl, and the like. A C1–C6 lower alkyl is preferred.

The "alkyl" portion of the term "alkoxy" means an alkyl as defined above, for example, methoxy, ethoxy, propoxy, t-butoxy, and the like.

The term "alkenyl" means a C2–C20 straight or branched alkenyl, for example, vinyl, allyl, propenyl, butenyl, pentenyl, hexenyl, heptenyl, and the like. A C2–C7 lower alkenyl is preferred.

The term "aryl" means phenyl or naphthyl. Examples of an optionally substituted aryl include, for example, 3,5-dichlorophenyl, 2,4-difluorophenyl, 3,5-difluorophenyl, 3,5-dimethylphenyl, 3,5-dimethoxyphenyl, 2,4,6-trimethylphenyl, 3,5-di-t-butylphenyl, 4-methoxyphenyl, 4-benzylphenyl, 4-hydroxyphenyl, 3,5-dinitrophenyl, 3-nitrophenyl, 3,5-diaminophenyl, 3-aminophenyl, and the like.

The term "heteroaryl" means a 5–7 membered heterocyclic group containing at least one hetero atom (N, O, or S), for example, pyridyl (e.g., 4-pyridyl), pyrimidinyl (e.g., 2-pyrimidinyl), pyridazinyl (e.g., 3-pyridazinyl), pyrazinyl (e.g., 2-pyrazinyl), thienyl (e.g., 2-thienyl), quinolyl (e.g., 3-quinolyl), imidazolyl (e.g., 2-imidazolyl), oxazolyl (e.g., 2-oxazolyl), thiazolyl (e.g., 5-thiazolyl), and the like. Pyridlyl is preferred.

The term "heteroarylalkyl" means the above defined alkyl substituted with the above defined heteroaryl, for example, pyridylmethyl (e.g., 4-pyridylmethyl), pyridylethyl (e.g., 1- or 2-(2-pyridyl)ethyl), pyridylpropyl (e.g., 3-(2-pyridyl)propyl), thienylmethyl (e.g., 2-thienylmethyl), quinolylmethyl (e.g., 3-quinolylmethyl), imidazolylmethyl (e.g., 2-imidazolylmethyl), and the like.

The term "aralkyl" means the above defined alkyl substituted with the above defined aryl, for example, benzyl, phenethyl (e.g., 1-phenethyl), naphthylmethyl, naphthylethyl (e.g., 2-naphthylethyl), and the like.

The term "acyl" means an aliphatic or aromatic acyl, for example, acetyl, propionyl, pivaloyl, benzoyl, and the like.

The "optionally substituted carbamoyl" may optionally be mono- or di-substituted with a substituent as described below, for example, N-methylcarbamoyl, N,N-dimethylcarbamoyl, and the like.

The term "alkoxycarbonyl" refers to , for example, methoxycarbonyl, etboxycarbonyl, and the like.

The term "halogen" means fluoro, chloro, bromo, and iodo. Chloro or bromo is preferred.

The "optionally substituted amino" may optionally be mono- or di-substituted with a substituent as described below, for example methylamino, dimethylamino, and the like.

When each group as described above is substituted, the substituent refers to, for example, an alkyl (e.g., methyl and ethyl), a halogen (fluoro, chloro, bromo, and jodo), an acyl (e.g., acetyl and benzoyl), an alkenyl (e.g., allyl), a cycloalkyl (e.g., cyclopropyl), an aralkyl (e.g., benzyl), an optionally substituted amino (e.g., methylamino and dimethylamino), hydroxy, oxo, an alkoxy (e.g., methoxy and ethoxy), cyano, carboxy, an alkoxycarbonyl (e.g., methoxycarbonyl), nitro, an acyloxy (e.g., acetyloxy). an optionally substituted carbamoyl (e.g., N-methylcarbamoyl), an optionally substituted carbamoyloxy (e.g., N-ethylcarbamoyloxy), and the like. One or more substituent(s) may be at any substitutable position(s). When the substituent interferes the reaction, a protective group may be introduced before the reaction, and then removed at any suitable step after the reaction.

The compound of the formula (I), the starting materials of the present invention, includes known ones and may be produced according to the method described in the International Patent Publication WO 96/10019 and the Japanese Patent Unexamined Publication 116242/1994. The compound of the formula (I) to be used in the present invention is, for example, 2-benzyloxymethyl-4-isopropylimidazole, 2-benzyloxymethyl-4-isopropyl-{1-(4-pyridylmethyl)}imidazole, 2-acetyloxymethyl-4-isopropyl-{1-(4-pyridylmethyl)}-imidazole, 2-benzoyloxymethyl-4-isopropyl-{1-(4-pyridlylmethyl)}-imidazole, 2-methoxycarbonyloxymethyl-4-isopropyl-{1-(4-pyridylmethyl)}-imidazole, 2-carbamoyloxymethyl-4-isopropyl-{1-(4-pyrid(ylmethyl)}-imidazole, and the like.

The compound (II) is commercially available or produced by reacting the corresponding disulfide $(R^4—S)_2$ wherein $R^4$ is an optionally substituted aryl, which is produced in accordance with known methods, with chlorine gas. The disulfide is, for example, bis(3,5-dichlorophenyl)disulfide, bis(4-chlorophenyl)disulfide, bis(2-chlorophenyl)disulfide, bis(4-nitrophenyl)disulfide, bis(2-nitrophenyl)disulfide, bis(2,4-dinitrophenyl)disulfide, bis(4-methoxyphenyl)disulfide, bis(4-methylphenyl)disulfide, bis(2,4,6-trimethylphenyl)disulfide, diphenyldisulfide, and the like. The amount of chlorine gas to be used in the preparation of the compound (II) is 1–3 mole equivalents to the disulfide $(R^4—S)_2$. The reaction may be carried out by introducing chlorine gas at 30–60° C. into an organic solvent (e.g., tetrachloromethane, chloroform, dichloromethane, toluene) in which a suitable amount of disulfide is dissolved.

The compound (II) is, for example, 3,5-dichlorobenzenesulfenyl chloride, 4-chlorobenzenesulfenyl chloride, 2-chlorobenzenesulfenyl chloride, 4-nitrobenzenesulfenyl chloride, 2-nitrobenzenesulfenyl chloride, 2,4-dinitrobenzenesulfenyl chloride, 4-methoxybenzenesulfenyl chloride, 4-methylbenzenesulfenyl chloride, 2,4,6-trimethylbenzenesulfenyl chloride, and the like.

A base to be used for the reaction of the compound (I) with the compound (II) is, for example, triethylamine, N-methylmorpholine, pyridine, N,N-dimethylaniline, N,N-diisopropyl-N-ethylamine, butyl lithium, diazabicycloundecene, and the like. A solvent is, for example, acetonitrile, toluene, dichloromethane, chloroform, dimethylformamide, nitromethane, benzene, tetrahydrofuran, and the like.

In the reaction of the present invention, the amount of a base is 0.1–3 mole equivalents, preferably 1–2 mole equivalents to the compound (I) and the amount of the compound (II) is 1–3 mole equivalents, preferably 1–2 mole equivalents to the compound (I). The reaction temperature can be −30–60° C., preferably 0–10° C. The reaction time can be 0.5–24 hours, preferably 0.5–3 hours. The compound (1) can be generally added to the compound (II) with stirring and vice versa. A base is either mixed with compound (I) in advance, or added at the end.

The following examples are provided to further illustrate the present invention and are not to be construed as limiting the scope thereof.

The meanings of the following abbreviations in the examples are shown below.

| | |
|---|---|
| Me | methyl |
| Ph | phenyl |
| Bn | benzyl |
| TEA | triethylamine |
| DMF | N,N-dimethylformamide |

REFERENCE EXAMPLE 1

3,5-Dichlorobenzenesulfenyl chloride (2)

Bis(3,5-dichlorophenyl)disulfide 15.0 g (42.1 mmol) was dissolved in tetrachloromethane (60 ml). The solution was added dropwise to a solution of chloride gas 9.0 g (126.9 mmol) in tetrachloromethane (50 ml) at −10° C. The mixture was kept standing 20 min at the same temperature, to which the dried nitrogen gas was bubbled for removing excessive chlorine. The resulting mixture was concentrated under reduced pressure to yield the objective (2) 18.6 g (quantitative) as a red oil.

$^1$H-NMR (CDCl$_3$-TMS) δ ppm: 7.32 (t, J=1.8 Hz, 1H), 7.43 (d, J=1.8 Hz, 2H)

REFERENCE EXAMPLE 2

3,5-Dichlorobenzenesulfenyl chloride (2)

Bis(3,5-dichlorophenyl)disulfide 30.0 g (84.2 mmol) was dissolved in toluene (90 ml). To the solution was introduced chlorine gas 11.9 g (167.8 mmol) under ice-cooling for 1 hour. The dried nitrogen gas was bubbled into the mixture at the same temperature for removing excessive chlorine to yield the toluene solution of the objective (2). Yield 99.7%.

EXAMPLE 1

2-Benzyloxymethyl-5-(3,5-dichloropbenylthio)-4-isopropyl-1H-imiidazole (3)

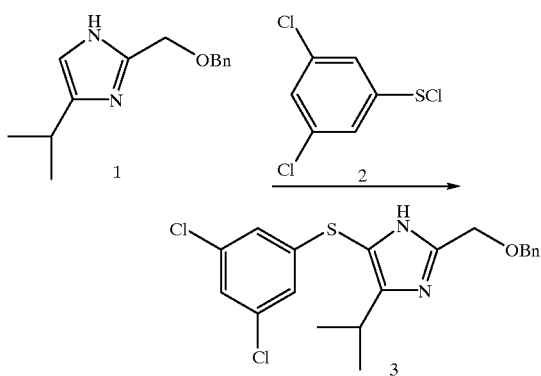

2-Benzyloxymethyl-4-isopropyl-1H-imidazole (1) 550 mg (2.4 mmol), described as a reference example 1 in WO 96/10019, was dissolved in the mixture of triethylamine 360 mg (3.6 mmol) and acetonitrile 4 ml. To the solution was added 3,5-dichlorobenzenesulfenyl chloride (2) 930 mg (4.4 mmol) at, room temperature. The mixture was stirred for 30 minutes at room temperature and water 15 ml and toluene 15 ml were added thereto. The toluene layer was separated, washed with water 10 ml twice, and concentrated under reduced pressure. The obtained yellow oil was crystallized with dilsopropyl ether 10 ml, filtered, and dried to yield the objective (3) 800 mg as a pale yellow crystal. Yield 82%.

$^1$H-NMR (CDCl$_3$-TMS) δ ppm: 1.22 (d, J=7.2Hz, 6H), 3.64 (sept, 1H), 4.62 (s, 2H), 4.67 (s, 2H), 6.92 (bs, 2H), 7.07 (bs, 1H), 7.36 (s, 5H), 9.20 (b, 1H).

EXAMPLE 2

2-Benzyloxmethl-5-(3,5-dichlorophenylthio)-4-isopropyl-1-pyrilin-4-yl)methyl-1H-imidazole (5)

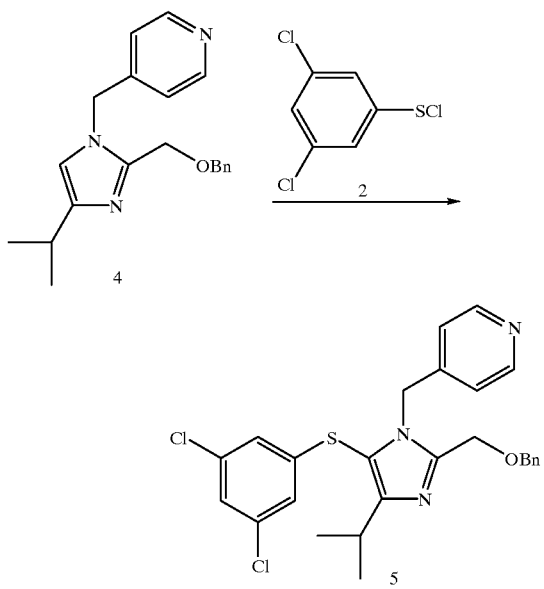

2-Benzyloxymethyl-4-isopropyl-1-(pyridin-4-yl)-1H-imidazole (4) 10.0 g (31.1 mmol) was dissolved in toluene (50 ml). The solution was added dropwise to a toluene solution 24.7 g of 3,5-dichlorobenzenesulfenyl chloride (2) 8.0 g (37.05 mmol) under ice-cooling for 30 minutes. To the mixture was added dropwise triethylamine 3,5 g (34.6 mmol) under ice-cooling for 1 hour, and the mixture was stirred at, the same temperature for 1.5 hour. To the mixture was added water 25 ml, and toluene layer was ejarated. The toluene layer was washed with water 25 ml, and each aqueous layer was extracted with toluene 10 ml. The toluene layer was collected, concentrated un(der reduced pressure, crystallized with diusopropyl ether 50 ml, filtered, and dried to the objective (5) 12.6 g as a pale yellow crystal. Yield 81.3%.

$^1$H-NMR (CDCl$_3$) δ ppm: 1.30 (d, J=7.2 Hz, 6H), 3.08–3.22 (m, 1H), 4.52 (s, 2H, 4.62 (s, 2H) 5.16 (s, 2H), 6.65 (d, J=1.8 Hz, 2H), 6.79 (d, J=6.0 Hz, 2H), 7.03 (t, J=1.8 Hz, 1H), 7.18–7.36 (m, 5H), 8.38 (d, J=6.0 Hz, 2H).

REFERENCE EXAMPLE 3

2-Acetyloxymethyl-4-isopropyl-1-(pyridin-4-yl)methyl-1H-imidazole (7a)

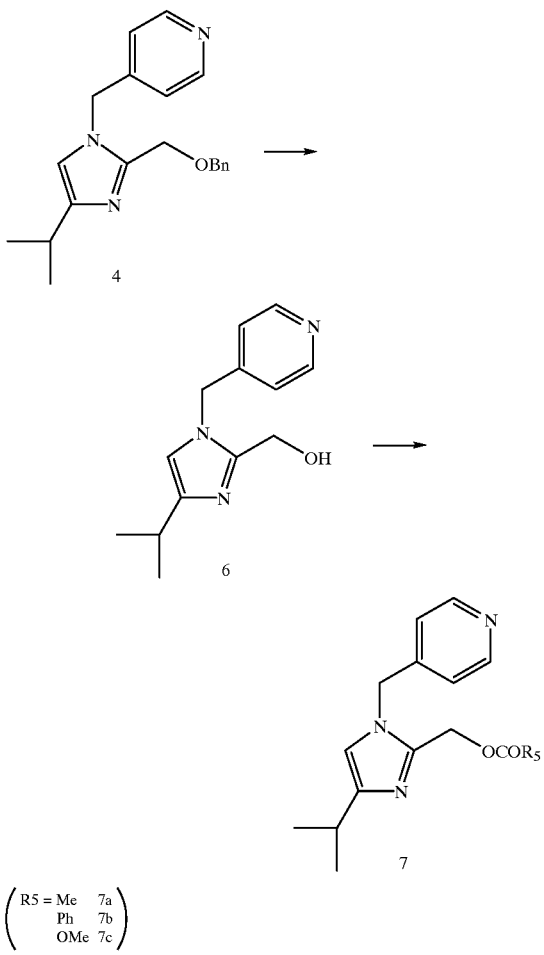

The compound (4) 20.0 g (62.2 mmol) was suspended in 35% aqueous hydrochloric acid 100 ml. The solution was heated at 85° C. and stirred for 1 hour. The reaction mixture was cooled down to room temperature, and water 100 ml and toluene 44 ml were added thereto. The aqueous layer was separated, neutralized with aqueous 30% sodium hydroxide, and stirred after addition of ethyl acetate 30 ml. The obtained slurry was filtered, washed with cold water, and dried to yield 2-hydroxymethyl-4-isopropyl-1-(pyridin-4-yl)-1H-imidazole (6) 11.7 g. Yield 81.4%.

$^1$H-NMR (CDCl$_3$) δ ppm: 1.16 (d, J=7.0 Hz, 6H), 2.68–2.89 (m, 1H), 4.59 (s, 2H), 5.23(s, 2H), 6.51 (s, 1H), 7.03 (d, J=6.0 Hz, 2H), 8.55 (d, J=6.0 Hz, 2H).

To a solution of the above-obtained hydroxy compound (6) 3.49 g (15 mmol), dichloromethane 35 ml, and triethylamine 1.83 g (18 mmol) was added dropwise acetylchloride 1.32 g (17 mmol) under ice-cooling and the mixture was stirred for 1 hour under ice-cooling. Water was added thereto, and the dichloromethane layer was separated, concentrated, and purified by column chromatography on silica gel (elution ethyl acetate: methanol=10:1) to yield the objective (7a) 3.34 g. Yield 81.1%.

$^1$H-NMR (CDCl$_3$) δ ppm: 1.26 (d, J=7.0 Hz, 6H), 1.85 (s, 3H), 2.88–3.05 (m, 1H), 5.11 (s, 2H), 5.15 (s, 2H), 6.64 (s, 1H), 6.95 (d, J=6.0 Hz, 2H), 8.59 ((d, J=6.0 Hz, 2H.

In accordance with the same method described above, the above-obtained hydroxy compound (6) 1.16 g (5 mmol), dichloromethane 12 ml, triethylamine 0.86 g (8.5 mmol), and benzoylchloride 1.16 g (8.3 mmol) were reacted to yield the objective (7b) 1.65 g. Yield 93.2%. (elution: ethyl acetate)

$^1$H-NMR (CDCl$_3$) δ ppm: 1.34 (d, J=7.0 Hz, 6H), 2.90–3.10 (m, 1H), 5.29 (s, 2H), 5.45 (s, 2H), 6.74 (s, 1H), 6.99 (d, J=6.0 Hz, 2H), 7.30–7.90 (m, 5H), 8.55 (d, J=6.0 Hz, 2H).

In accordance with the same method described above, the above-obtained hydroxy compound (6) 1.16 g (5 mmol), dichloromethane 12 ml, triethylamine 0.76 g (7.5 mmol). and methyl chloroformate 0.70 g (7.4 mmol) were reacted to yield the objective (7c), methoxycarbonyloxy derivative, 0.40 g. Yield 27.6%.

$^1$H-NMR (CDCl$_3$) δ ppm: 1.25 (d, J=7.0 Hz, 6H), 2.80–3.00 (m, 1H), 3.70 (s, 3H), 5.17 (s, 2H), 5.18 (s, 2H), 6.64 (s, 1H), 6.97 (d, J=6.0 Hz, 2H), 8.59 (d, J=6.0 Hz, 2H).

EXAMPLE 3

2-Acetyloxymethyl-5-(3,5-dichlorophenylthio)-4-isopropyl-1-(pyridin-4-yl)methyl-1H-imidazole (8)

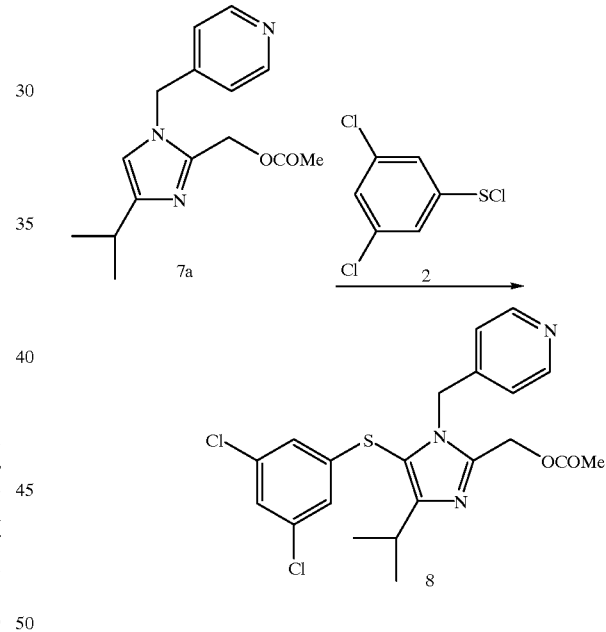

To a toluene solution 1.88 g of the compound (2) 0.97 g (4.5 mmol) was added dropwise an acetonitrile solution 4 ml of the compound (7a) 0.87 g (3.2 mmol) under ice-cooling for 30 minutes. The solution of triethylamine 0.46 g (4.5 mmol) and acetonitrile 0.5 ml was added dropwise thereto for 15 minutes, and the mixture was stirred under ice-cooling for 2 hours. The reaction mixture was concentrated under reduced pressure and extracted with ethyl acetate. The extract was washed with water, concentrated under reduced pressure, and purified by column chromatography on silica gel (elution ethyl acetate) to yield the objective (8) 1.17 g as a crystal. Yield 82%. Mp 133–135° C.

$^1$H-NMR (CDCl$_3$-TMS) δ ppm: 1.31 (d, J=6.0 Hz, 6H), 1.85 (s, 3H), 3.18–3.30 (m, 1H), 5.18 (s, 2H), 5.19 (s, 2H) 6.69 (d, J=2.0 Hz, 2H), 6.78 (d, J=6.0 Hz, 2H), 7.05 (d, J=2.0 Hz, 1H), 8.45 (d, J=6.0 Hz, 2H).

REFERENCE EXAMPLE 4

2-Hydroxymethyl-5-(3,5-dichlorophenyithio)-4-isopropyl-1-(pyridin-4-yl)methyl-1H-imidazole (9)

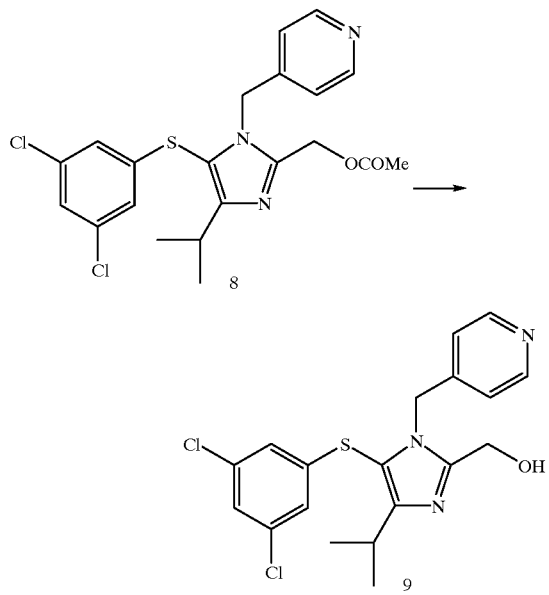

To an ethanol suspension 3.5 ml of the compound (8) 0.35 g (0.77 mmol) obtained in example 3 was added 1N aqueous sodium hydroxide 0.82 ml. The reaction mixture was stirred for 30 minutes, concentrated under reduced pressure, and extracted with ethyl acetate. The extract was washed with water and concentrated under reduced pressure to yield the objective (9) 0.31 g. Yield 96.9%.

REFERENCE EXAMPLE 5

2-Carbamoyloxymethyl-4-isopropyl-1-(pyridin-4-yl)methyl1H-imiidazole (10)

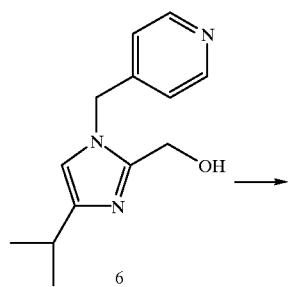

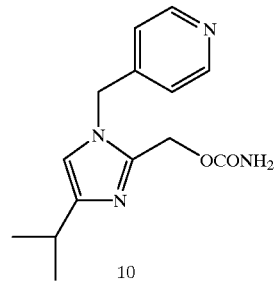

The hydroxy compound (6) 15.0 g (64.9 mmol) was suspended in acetonitrile 150 ml. To the solution was added dropwise anhydrous hydrochloric acid 5.2 g (142.5 mmol) in ethyl acetate 42 ml at room temperature. The mixture was cooled down to 0° C. under nitrogen atmosphere, and chlorosulfonyl isocyanate 22.0 g (155.4 mmol) was added thereto under cooling for 45 minutes. The reaction mixture was stirred at the same temperature for 1 hour, and water 13.5 ml and 35% aqueous hydrochloric acid 13.5 ml were added thereto. The mixture was stirred at 45° C. for 1 hour, cooled down to room temperature, and neutralized by 20% aqueous sodium carbonate. The mixture was kept stationary and separated. The organic layer was washed with water, and the aqueous layer was extracted with ethyl acetate. The organic layer was collected, concentrated, and dried. To the residue was added diusopropyl ether 80 ml, and the solution was stirred for 1 hour at room temperature. The obtained slurry was filtered. washed with dilsopropyl ether, and dried to yield the objective (10) 14.8 g (yield 83.2%).

$^1$H-NMR (CDCl$_3$-TMS) δ ppm: 1.25 (d, J=7.0 Hz, 6H), 2.80–3.00 (m, 1H), 4.95 (bs, 2H), 5.10 (s, 2H), 5.20 (s, 2H), 6.63 (s, 1H), 6.97 (d, J=5.2 Hz, 2H), 8.57 (d, J=5.0 Hz, 2H).

EXAMPLE 4

2-Carbamoyloxymethyl-5-(3,5-dichlorophenylthio)-4-isopropyl-1-(pyridin-4-yl)methyl-1H-imidazole (11)

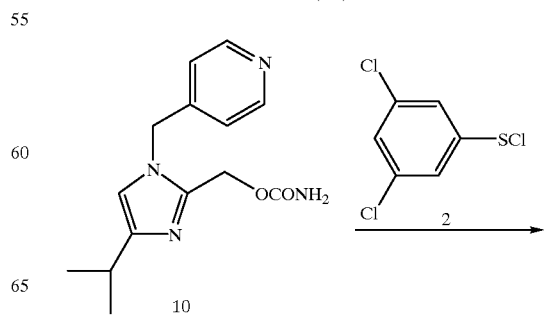

-continued

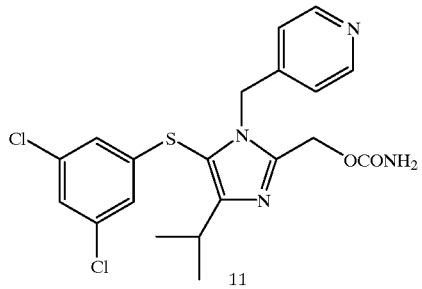

The compound (10) 250 mg (0.91 mmol) was dissolved in N,N-dimethylformamide 4 ml. The solution was cooled down to −30° C. under nitrogen atmosphere. To the solution were added alternately four times a toluene solution 150 mg of the compound (2) 77 mg (0.36 mmol) and a toluene solution 150 mg of triethylamine 36 mg (0.36 mg), and additionally added a toluene solution 150 mg of the compound (2) 77 mg (0.36 mmol). The reaction mixture was stirred at −30° C. for 30 minutes, and ethyl acetate and aqueous sodium hydrogen carbonate were added thereto. The objective (11) was extracted with ethyl acetate. Diluted aqueous hydrochloric acid was added thereto, and the objective was re-dissolved in aqueous layer. The aqueous solution was neutralized by aqueous sodium hydrogen carbonate and extracted with ethyl acetate. The extract was dried over anhydrous sodium sulfate and concentrated under reduced pressure to prepare oily residue. The oily residue was dissolved in methanol 0.9 ml, and water 0.7 ml was added for 1–2 minutes at, room temperature thereto to prepare the precipitate. The suspension was stirred for 30 minutes at room temperature, additionally stirred for 30 minutes under ice-cooling, filtered, washed with 50% aqueous methanol, and dried to yield the objective (11) 250 mg as a white crystal. Yield 61%. mp 88° C. (dec)

$^1$H-NMR (CDCl$_3$-TMS) δ ppm: 1.32 (d, J=6.9Hz, 6H), 3.17 (sept, 1H), 4.53 (b, 2H), 5.21 (s, 2H), 5.27 (s, 2H), 6.69 (d, J=1.6 Hz, 2H), 6.82 (d, J=5.2 Hz, 2H), 7.06 (t, J=1.6 Hz, 1H), 8.46 (b, 2H). Element analysis (C$_{20}$H$_{20}$Cl$_2$N$_4$O$_2$S.0.5H$_2$O); Calcd. (%): C, 52.16: H, 4.61: N, 12.17: S, 6.96: Cl, 15.42; Found.(%): C, 52.45: H, 4.72: N, 11.73: S, 7.08: Cl, 14.81; 2HCl salt of the compound (11): mp 214–222° C. (dec)

REFERENCE EXAMPLE 6

(I) 2,2-Dichloro-3-methylbutylaldehyde (13)

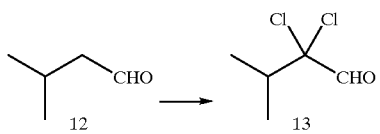

To the mixture of isovalelaldehyde (12) 192 g (2.23 mol) and N,N-dimethylformamide 230 ml was introduced chlorine 316 g (4.46 mol) under 60° C. The mixture was cooled down, mixed with water 384 ml, and separated. The organic layer was washed with aqueous sodium hydrogen carbonate 350 g, and each aqueous layer was extracted with toluene 115 ml. The organic layer was collected to yield the toluene solution 440 g of the objective (13). (Yield 75%).

$^1$H-NMR (CDCl$_3$-TMS) δ ppm: 1.15 (d, J=6.6 Hz, 6H), 2.56 (sept, J=6.6 Hz, 1H). 9.24 (s, 1H).

(II) 1,4-Dibenzyloxy-2-butene (15)

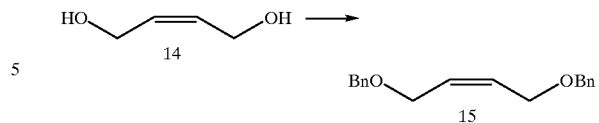

To 48% aqueous sodium hydroxide 127.8 g was added tetra-n-butylammonium bromide 3.3 g (10 mmol), and the mixture was heated to 60° C. To the mixture was added 2-butene-1,4-diol (14) 30.0 g (340 mmol), to which was added dropwise benzyl chloride 94.8 g (743 mmol) at 80±15° C. The mixture was stirred at the same temperature for 2 hours. The reaction mixture was cooled down, and separated after addition of water 90 ml. To the organic layer was add sulfuric acidic brine. The solution was neutralized by aqueous sodium hydrogen carbonate, separated, mixed with ethyl acetate, and concentrated under reduced pressure to yield the oil residue 104.5 g (quantitative) of the objective (15).

$^1$H-NMR (CDCl$_3$-TMS) δ ppm: 4.05 (d, J=3.8 Hz, 2H), 4.48 (s, 2H), 5.78 (m, 2H), 7.31 (m, 10H).

Benzyloxyacetoaldehyde (16)

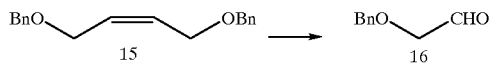

1,4-Dibenzyloxy-2-butene (15) 104.5 g (340 mmol) obtained above was dissolved in methanol 1458 ml. The solution was cooled down to −60° C. under nitrogen atmosphere. Ozone was introduced thereto at −60° C. until the starting material was disappeared, and then the excess amount of ozone gas was removed by bubbling nitrogen gas. To the solution was added dropwise an ethyl acetate solution 550 ml of triphenylphosphine 107.2 g (409 mmol) at −60° C. to reduce the reaction intermediate. The reaction mixture was warmed to room temperature, and concentrated under reduced pressure to yield the oily mixture 321.6 g (quantitative) of phosphorous compound and the objective (16).

(III) 2-Benzyloxymethyl-4-isopropyl-1H-imidazole (17)

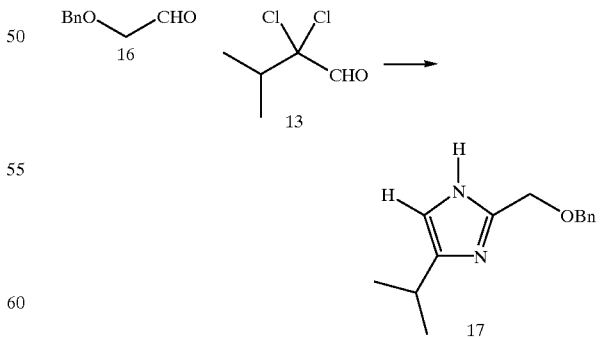

The oil residue 268 g (approximately 0.57 mol) obtained in (II) of the benzyloxy acetaldehyde (16) and the extract 183 g (0.70 mol) obtained in (I) of 2,2-dichloro-3-methylbutylaldehyde (13) were mixed with acetonitrile 276 ml. 25% aqueous ammonia was added thereto. The mixture was stirred at 45° C. for 8 hours, extracted with toluene 213 ml and separated to yield the extract, 725 g (yield 70%) of the objective (17). The compound (17) can be crystallized by hexane.

$^{1}$H-NMR (CDCl$_{3}$-TMS) δ ppm: 1.23 (d, J=6.8 Hz, 6H), 2.88 (sept, J=6.8 Hz, 1H), 4.51 (s, 2H), 4.58 (s, 2H), 6.65 (d, J=1.0 Hz, 1H), 7.1–7.4 (m, 5H).

(IV) 4-Chloromethylpyridine hydrochloride (19)

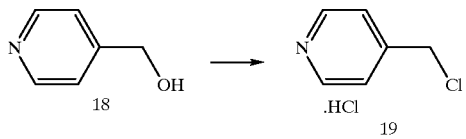

4-Hydroxymethylpyridine (18) 54.4 g (0.50 mol) was dissolved in acetonitrile 202 ml. The solution was added dropwise to the mixture of thionyl chloride 65.3 g (0.55 mol) and acetonitrile 109 ml under 50° C. The mixture was stirred at the same temperature for 1 hour, then cooled to room temperature to yield the slurry (quantitative) of the objective (19).

$^{1}$H-NMR (DMSO-TMS) δ ppm: 5.09 (s, 2H), 8.09 (d, J=6.6 Hz, 2H), 8.94 (d, J=6.6 Hz, 2H), (V) 2-Benzyloxymethyl-4-isopropyl-1-(pyridin-4-yl)methyl-1H-imidazole 2nitrate (20)

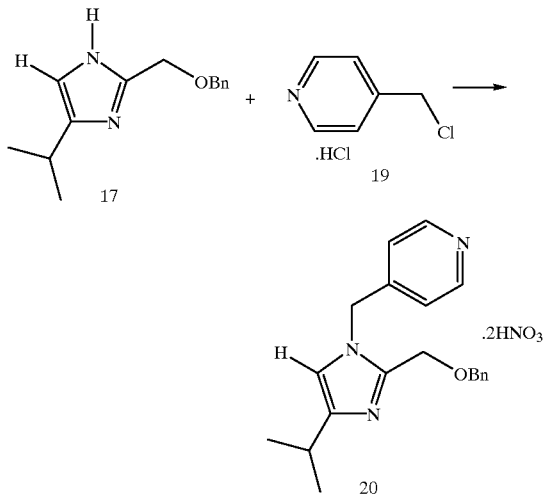

The extract 725 g (approximately 0.40 mol) obtained in (III) of 2-benzyloxymethyl-4-isopropyl-1H-imidazole (17) was neutralized by aqueous sulfuric acid, mixed with the slurry (approximately 0.50 mol) obtained in (IV) of 4-chloromethylpyridine hydrochloride (19) and water, and then alkalified by aqueous sodium hydroxide. The mixture was separated, the aqueous layer was extracted with toluene 65 ml, and the organic layer was collected. The organic layer was concentrated to 830 ml, mixed with sodium hydroxide 62.6 g, and stirred at 40° C. for 5 hours. The reaction mixture was mixed with water 226 ml and separated. The aqueous layer was extracted with toluene 65 ml, and the organic layer was collected. The organic layer was mixed with 20% aqueous sulfuric acid 348 g and the aqueous layer was separated. The organic layer was extracted with water 65 ml, and the aqueous layer was collected. The aqueous layer was mixed with 20% aqueous sodium hydroxide 282 g and extracted with ethyl acetate 130 ml. The organic layer was washed with brine, and each aqueous layer was extracted with ethyl acetate 65 ml. The organic layer was collected, concentrated under reduced pressure, and dried. The residue was mixed with ethyl acetate 523 ml and methanol 131 ml, crystallized by concentrated sulfuric acid 82.9 g (0.89 mol), filtered, and dried to yield the objective (20) 161.3 g as a pale yellow crystal. Yield 90%. mp 155° C. (dec).

The free compound of the objective (20) can be crystallized by diisopropyl ether.

$^{1}$H-NMR (CD$_{3}$OD-TMS) δ ppm: 1.34 (d, J=7.0 Hz, 6H), 3.08 (sept, J=7.0 Hz, 1H), 4.86 (s, 2H), 4.89 (s, 2H), 5.78 (s, 2H), 7.16 (m, 2H), 7.28 (m, 2H), 7.49 (d, J=1.0 Hz, 1H), 7.74 (d, J=6.8 Hz, 2H), 8.67 (d, J=6.8 Hz, 2H).

2-Benzyloxymethyl-5-(3,5-dichlorophenylthio)-4-isopropyl-1-pyridin-4-yl)methyl-1H-imidazole (5)

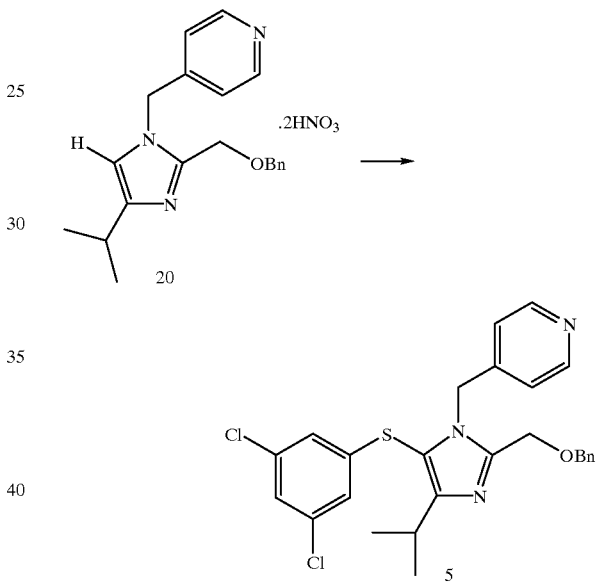

2-Benzyloxymethyl-4-isopropyl-1-pyridin-4-yl)-1H-imidazole 2 nitrate (20) 13.9 g (31 mmol) was suspended in toluene 50 ml and water 12 ml. The solution was neutralized by 30% aqueous sodium hydroxide. The toluene layer was washed with water 40 ml, concentrated, and dried. The residue was dissolved in toluene 50 ml. The solution was added dropwise to toluene solution 24.7 g of 3,5-dichlorobenzenesulfenylchloride (2) 7.9 g (37 mmol). To the mixture was added dropwise triethylamine 3.5 g (34 mmol) under ice-cooling for 1 hour. The mixture was stirred at the same temperature for 2.5 hours, and mixed with water 25 ml. The toluene layer was separated and washed with water 25 ml, and the aqueous layer was re-extracted with toluene 10 ml. The toluene layer was collected and concentrated under reduced pressure. The residue was crystallized by dilsopropyl ether, filtered, and dried to yield the objective (5) 13.0 g as a pale yellow crystal. Yield 84%.

$^{1}$H-NMR (CDCl$_{3}$) δ ppm: 1.30 (d, J=7.2 Hz, 6H), 3.08–3.22 (m, 1H), 4.52 (s, 2H), 4.62 (s, 2H) 5.16 (s, 2H), 6.65 (d, J=1.8 Hz, 2H), 6.79 (d, J=6.0 Hz, 2H), 7.03 (t, J=1.8 Hz, 1H), 7.18–7.36 (m, 5H), 8.38 (d, J=6.0 Hz, 2H).

2-Hydroxymethyl-5-(3,5-dichlororhenylthio)-4-isopropyl-1-(pyridin-4-yl)methyl-1H-imidazole (9)

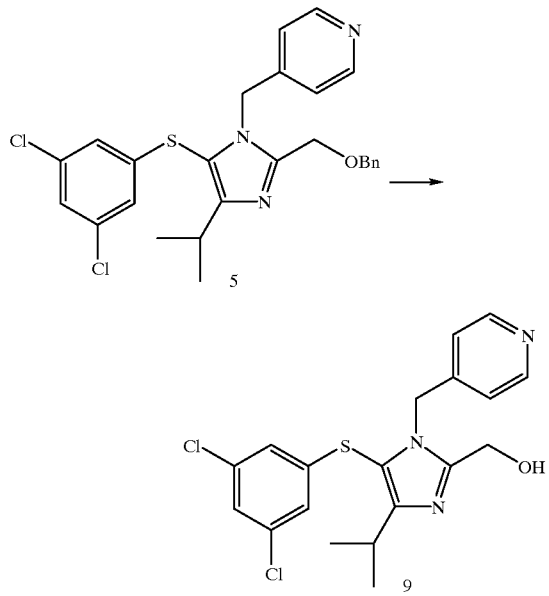

To the compound (5) was added aqueous concentrated hydrochloric acid 50 ml. The mixture was heated at 90° C. for 2 hours and then cooled down. To the mixture were added water 50 ml and toluene 20 ml. The aqueous layer was separated and neutralized by 30% aqueous sodium hydroxide. The compound (9) was extracted with ethyl acetate 50 ml, and the ethyl acetate layer was washed with water 30 ml. Each aqueous layer was extracted with ethyl acetate 20 ml. The ethyl acetate layer was collected and concentrated under reduced pressure to yield oily residue. To the oily residue was slowly added diisopropyl ether 50 ml. The obtained slurry was stirred at room temperature for 30 minutes, filtered, washed with diusopropyl ether 30 ml, and dried to yield the compound (9) 10.4 g as a white crystal. Yield from the compound (20): 82

2-Carbamoyloxymethyl-5-(3,5-dichloroihenylthio)-4-isopropyl-1-(pyridin-4-yl)methyl-1H-imidazole (11)

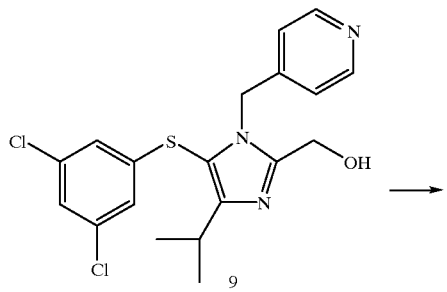

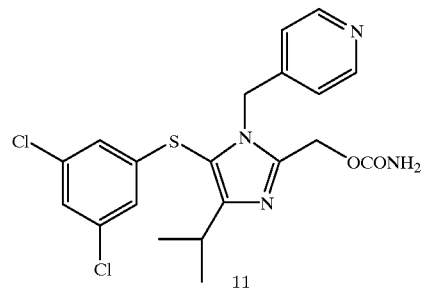

The hydroxy compound (9) 2.00 g (4.9 mmol) was suspended in ethyl acetate 20 ml, and the solution was cooled down to −30° C. under nitrogen atmosphere. To the solution was added dropwise chlorosulfonyl isocyanate 1.66 g (11.4 mmol) under nitrogen atmosphere at −30° C. for 30 minutes, and the mixture was stirred at the same temperature for 1 hour. To the mixture was added dropwise water 2 ml, and the mixture was warmed up to 0° C. To the mixture were added 35% aqueous hydrochloric acid 2 ml and methanol 4 ml, and the solution was stirred at 40° C. for 1 hour. The mixture was cooled down to room temperature and neutralized by 20% aqueous sodium carbonate. The organic layer was separated, washed with water, concentrated, and dried. To the residue was added methanol 6 ml and after that water 6 ml at room temperature. The obtained slurry was filtered, washed with 50% aqueous methanol 6 ml, and dried to yield the compound (11) 2.06 g (yield 93.2%).

$^1$H-NMR (CDCl$_3$-TMS) δ ppm: 1.32 (d, J=6.9 Hz, 6H), 3.17 (sept, 1H), 4.53 (b, 2H), 5.21 (s, 2H), 5.27 (s, 2H), 6.69 (d, J=1.6 Hz, 2H), 6.82 (d, J=5.2 Hz, 2H) 7.06 (t, J=1.6 Hz, 1H), 8.46 (b, 2H). Element analysis (C$_{20}$H$_{20}$Cl$_2$N$_4$O$_2$S.0.5H$_2$O ); Calcd. (%): C, 52.16: H, 4.61: N, 12.17: S, 6.96: Cl, 15.42; Found. (%): C, 52.45: H, 4.72: N, 11.73: S, 7.08: Cl, 14.81; 2HCl salt of the compound (11): mp 214–222° C. (dec)

EXAMPLES 5–6

Compounds described blow were produced in the same manner as described above to establish reaction conditions.

TABLE 1

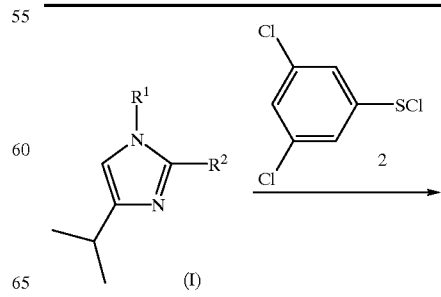

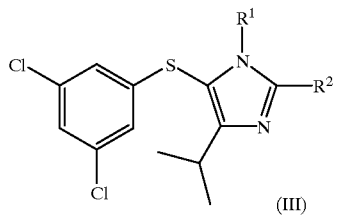

(III)

| Example No. | $R^1$ | $R^2$ |
|---|---|---|
| 1 | H | $CH_2OBn$ |
| " | " | " |
| 2 | $CH_2$-4-pyridyl | " |
| 3 | " | $CH_2OCOMe$ |
| 4 | " | $CH_2OCONH_2$ |
| 5 | " | $CH_2OCOPh$ |
| 6 | " | $CH_2OCOOMe$ |

TABLE 2

| Example No. | Compound 2 mol eq. | TEA mol eq. | Solvent | Reaction temperature (° C.) | Reaction time (hour) | Yield (%) |
|---|---|---|---|---|---|---|
| 1 | 1.8 | 1.5 | $CH_3CN$ | r.t. | 0.5 | 82 |
| " | 1.8 | 1.5 | toluene | 50–55 | 2.5 | 82 |
| 2 | 1.2 | 1.1 | toluene | 0–5 | 2.0 | 81 |
| 3 | 1.4 | 1.4 | $CH_3CN$ | 0–5 | 2.0 | 82 |
| 4 | 2.0 | 1.6 | DMF | 30 | 0.5 | 61 |
| 5 | 1.4 | 1.2 | $CH_3CN$ | 0–5 | 2.0 | 85 |
| 6 | 1.4 | 1.2 | $CH_3CN$ | 0–5 | 1.0 | 83 |

INDUSTRIAL APPLICABILITY

The present invention provides a process for producing imidazole derivatives (III) useful as an antiviral agent and an anti-HIV agent, which is applicable to convenient, economical production on a large scale.

We claim:

1. A process for producing a compound of the formula (III):

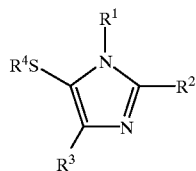

(III)

wherein $R^1$ and $R^3$ are independently hydrogen or an organic group; $R^2$ is an organic group; and $R^4$ is an optionally substituted aryl, which comprises reacting the compound of the formula (I):

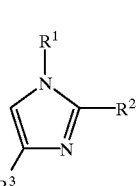

(I)

wherein $R^1$, $R^2$, and $R^3$ are as defined above, with a compound of the formula (II):

$R^4$—S—Hal (II)

wherein $R^4$ is as defined above and Hal is halogen, in the presence of a base.

2. The process as claimed in claim 1 wherein the organic group is an optionally substituted alkyl, an optionally substituted alkenyl, an optionally substituted aryl, an optionally substituted arylthio, an optionally substituted heteroaryl, an optionally substituted heteroarylalkyl, an optionally substituted aralkyl, an optionally substituted acyl, an optionally substituted carbamoyl, an optionally substituted alkoxycarbonyl. —CH=NOH, —CH=$NNH_2$, or —A—X wherein A is —$CH_2O$ $CH_2$— or —$CH_2O$— and X is an optionally substituted aryl or —$COR^5$ wherein $R^5$ is an optionally substituted alkyl, an optionally substituted alkoxy, an optionally substituted aryl, or an optionally substituted amino.

3. The process as claimed in claim 1 wherein $R^1$ is hydrogen or an optionally substituted heteroarylalkyl; $R^2$ is —A—X wherein A is —$CH_2O$ $CH_2$— or —$CH_2O$— and X is an optionally substituted aryl or —$COR^5$ wherein $R^5$ is an optionally substituted alkyl, an optionally substituted alkoxy, an optionally substituted aryl, or an optionally substituted amino; and $R^3$ is an optionally substituted alkyl.

4. The process as claimed in claim 1 wherein $R^1$ is an optionally substituted pyridylmethyl.

5. The process as claimed in claim 1 wherein a compound of the formula (II) is 3,5-dichlorobenzenesulfenyl chloride.

6. The process as claimed in claim 1 wherein said base is triethylamine or N-methylmorpholine.

* * * * *